United States Patent
Baaijens et al.

(10) Patent No.: US 9,526,860 B2
(45) Date of Patent: Dec. 27, 2016

(54) METHODS AND APPARATUS FOR PROVIDING PERSONALIZED LIGHTING

(71) Applicant: PHILIPS LIGHTING HOLDING B.V., Eindhoven (NL)

(72) Inventors: Johannes Petrus Wilhelmus Baaijens, Eindhoven (NL); Lucas Josef Maria Schlangen, Eindhoven (NL)

(73) Assignee: PHILIPS LIGHTING HOLDING B.V., Eindhoven (NL)

( * ) Notice: Subject to any disclaimer, the term of this patent is extended or adjusted under 35 U.S.C. 154(b) by 0 days.

(21) Appl. No.: 14/415,271

(22) PCT Filed: Jul. 4, 2013

(86) PCT No.: PCT/IB2013/055469
§ 371 (c)(1),
(2) Date: Jan. 16, 2015

(87) PCT Pub. No.: WO2014/013376
PCT Pub. Date: Jan. 23, 2014

(65) Prior Publication Data
US 2015/0174361 A1    Jun. 25, 2015

Related U.S. Application Data

(60) Provisional application No. 61/672,798, filed on Jul. 18, 2012.

(51) Int. Cl.
*H05B 37/00* (2006.01)
*A61M 21/02* (2006.01)
(Continued)

(52) U.S. Cl.
CPC ............ *A61M 21/02* (2013.01); *A61N 5/0618* (2013.01); *H05B 37/0209* (2013.01);
(Continued)

(58) Field of Classification Search
CPC ..................... A61M 2021/0044; A61M 21/00; A61M 2021/0083; A61M 2205/18; A61M 2205/3368; A61M 2205/3375; A61M 2205/50; A61M 2230/63; A61M 2205/3569; A61M 2205/3592; A61M 2205/507; A61M 2210/0612; A61N 2005/0653; A61N 5/0618; A61N 2005/0662; A61N 2005/0663; H05B 37/02

See application file for complete search history.

(56) References Cited

U.S. PATENT DOCUMENTS 7,348,736 B2    3/2008  Piepgras et al.
7,804,417 B2    9/2010  Fujikawa et al.
(Continued)

FOREIGN PATENT DOCUMENTS

DE    102010030501 A1    12/2010
WO         9000777 A1     1/1990
WO      2011089540 A1     7/2011

OTHER PUBLICATIONS

Sachin Bhardwaj et al, "Smart Lighting Using LED Luminaries", IEEE, pp. 654-659, 2010.

*Primary Examiner* — Monica C King
(74) *Attorney, Agent, or Firm* — Meenakshy Chakravorty

(57) ABSTRACT

Methods and apparatus that provide first lighting having first light output characteristics to a first user and simultaneously provide second lighting having second light output characteristics to a second user. The first lighting and the second lighting are distinct and may optionally be dynamic and responsive to lighting needs of the respective users.

15 Claims, 5 Drawing Sheets

(51) Int. Cl.
  *A61N 5/06* (2006.01)
  *H05B 37/02* (2006.01)
  *A61M 21/00* (2006.01)

(52) U.S. Cl.
  CPC ..... *H05B 37/0218* (2013.01); *H05B 37/0227* (2013.01); *A61M 2021/0044* (2013.01); *A61M 2205/3303* (2013.01); *A61M 2205/3576* (2013.01); *A61M 2205/502* (2013.01); *A61M 2205/84* (2013.01); *A61N 2005/0651* (2013.01)

(56) References Cited

U.S. PATENT DOCUMENTS

| | | | |
|---|---|---|---|
| 2008/0219013 A1* | 9/2008 | Budinger | A61N 5/0618 362/471 |
| 2010/0076250 A1 | 3/2010 | Van Wouldenberg et al. | |
| 2010/0241018 A1* | 9/2010 | Vogel | A61B 5/0002 600/511 |
| 2010/0277316 A1 | 11/2010 | Schlangen et al. | |
| 2011/0225532 A1 | 9/2011 | Isert et al. | |

\* cited by examiner methods and apparatus for providing personalized lighting

CROSS-REFERENCE TO PRIOR APPLICATIONS

This application is the U.S. National Phase application under 35 U.S.C. §371 of International Application No. PCT/IB2013/055469, filed on Jul. 4, 2013, which claims the benefit of U.S. Provisional Patent Application No. 61/672,798, filed on Jul. 18, 2012. These applications are hereby incorporated by reference herein.

TECHNICAL FIELD

The present invention is directed generally to lighting control and lighting apparatus. More particularly, various inventive methods and apparatus disclosed herein relate to providing dynamic personalized lighting adaptable to users' needs.

BACKGROUND

Various therapeutic lighting systems have been utilized. For example, therapeutic lighting systems have been utilized as therapy for seasonal depression, therapy for jetlag by flying, therapy for social jetlag, etc. Such therapeutic lighting systems often include a lighting fixture that a user must sit or stand in front of for a period of time for therapy purposes. Such therapeutic lighting systems may have one or more drawbacks such as, for example, the requirement of dedicated spaces or locations where the user has to sit down and/or stand for an extended period of time. Also, for example, the bright therapeutic light may be bothersome to other individuals present that do not need the light therapy. Also, for example, the therapeutic lighting systems may not offer dynamic personalized sections for multiple users.

Thus, there is a need in the art to provide methods and apparatus related to lighting control that may optionally be utilized to overcome one or more drawbacks of existing lighting systems, such as existing therapeutic lighting systems.

SUMMARY

The present disclosure is directed to inventive methods and apparatus for lighting. For example, methods and apparatus are disclosed that provide first lighting having first light output characteristics to a first user and simultaneously provide second lighting having second light output characteristics to a second user. The first lighting and the second lighting are distinct and may optionally be dynamic and responsive to lighting needs of the respective user.

Generally, in one aspect, a method of controlling lighting provided to multiple users is provided and includes: receiving first user lighting information indicative of lighting needs of a first user in a space; receiving second user lighting information indicative of lighting needs of a second user in the space; and providing first lighting having first light output characteristics to the first user and providing second lighting having second light output characteristics to the second user. The first lighting and the second lighting are distinct. The first lighting is dynamic and responsive to lighting needs of the first user as determined via the first user lighting information and the second lighting is dynamic and responsive to lighting needs of the second user as determined via the second user lighting information.

In some embodiments, the method further includes identifying a first location of the first user and directing the first lighting to the first user. In some versions of those embodiments the method further includes identifying a second location of the second user and directing the second lighting to the second user.

In some embodiments, the method further includes providing an indication of a first area of the first lighting in the predefined space to the first user. In some versions of those embodiments the providing of the indication of the first area of the first lighting includes transmitting the first location to a personal device of the first user. In some versions of those embodiments the method further includes providing an indication of a second area of the second lighting in the predefined space to the second user.

In various embodiments of the invention, the first lighting is distinct from the second lighting in at least one of intensity, spectral composition, angular distribution, angular direction, and dynamic behavior. The first lighting may be generated from a first group of LEDs and the second lighting may be generated from a second group of LEDs.

In some embodiments, the first user lighting information includes travel information of the first user and the first user lighting is configured to treat jetlag based on the travel information.

In some embodiments, the first user lighting information is transmitted from a mobile electronic device of the first user.

Generally, in another aspect, a method of controlling lighting to tailor the lighting to multiple users is provided and includes: providing first lighting having first light output characteristics to a first area in a room and providing second lighting having second light output characteristics to a second area in the room, wherein the first lighting and the second lighting are distinct; identifying lighting needs of a first user for the first light output characteristics; and directing the first user to the first area.

In some embodiments, the first light output characteristics include a first light output level that is greater than a second light output level of the second light output characteristics.

The method may further include providing a smoothly transitioning lighting between the first area and the second area, the smoothly transitioning lighting gradually transitioning differences between the first light output characteristics and the second light output characteristics. In some versions of those embodiments the first light output characteristics include a first light output level that is greater than a second light output level of the second light output characteristics. In some versions of those embodiments the method further includes identifying lighting needs of a second user for the second light output characteristics and directing the second user to the second location. In some versions of those embodiments the first lighting is dynamic and responsive to lighting needs of the first user as determined via the first user lighting information and the second lighting is dynamic and responsive to lighting needs of the second user as determined via the second user lighting information.

In some embodiments, the directing of the first user to the first area includes transmitting the first area to a personal device of the first user.

The method may further include identifying lighting needs of a second user for the second light output characteristics and directing the second user to the second location. In some versions of those embodiments the first lighting is dynamic and responsive to lighting needs of the first user as determined via the first user lighting information and the second lighting is dynamic and responsive to lighting needs of the second user as determined via the second user lighting information.

Other embodiments may include a non-transitory computer readable storage medium storing instructions executable by a processor to perform a method such as one or more of the methods described herein. Yet another implementation may include a system including memory and one or more processors operable to execute instructions, stored in the memory, to perform a method such as one or more of the methods described herein.

As used herein for purposes of the present disclosure, the term "LED" should be understood to include any electroluminescent diode or other type of carrier injection/junction-based system that is capable of generating radiation in response to an electric signal. Thus, the term LED includes, but is not limited to, various semiconductor-based structures that emit light in response to current, light emitting polymers, organic light emitting diodes (OLEDs), electroluminescent strips, and the like. In particular, the term LED refers to light emitting diodes of all types (including semi-conductor and organic light emitting diodes) that may be configured to generate radiation in one or more of the infrared spectrum, ultraviolet spectrum, and various portions of the visible spectrum (generally including radiation wavelengths from approximately 400 nanometers to approximately 700 nanometers). Some examples of LEDs include, but are not limited to, various types of infrared LEDs, ultraviolet LEDs, red LEDs, blue LEDs, green LEDs, yellow LEDs, amber LEDs, orange LEDs, and white LEDs (discussed further below). It also should be appreciated that LEDs may be configured and/or controlled to generate radiation having various bandwidths (e.g., full widths at half maximum, or FWHM) for a given spectrum (e.g., narrow bandwidth, broad bandwidth), and a variety of dominant wavelengths within a given general color categorization.

For example, one implementation of an LED configured to generate essentially white light (e.g., a white LED) may include a number of dies which respectively emit different spectra of electroluminescence that, in combination, mix to form essentially white light. In another implementation, a white light LED may be associated with a phosphor material that converts electroluminescence having a first spectrum to a different second spectrum. In one example of this implementation, electroluminescence having a relatively short wavelength and narrow bandwidth spectrum "pumps" the phosphor material, which in turn radiates longer wavelength radiation having a somewhat broader spectrum.

It should also be understood that the term LED does not limit the physical and/or electrical package type of an LED. For example, as discussed above, an LED may refer to a single light emitting device having multiple dies that are configured to respectively emit different spectra of radiation (e.g., that may or may not be individually controllable). Also, an LED may be associated with a phosphor that is considered as an integral part of the LED (e.g., some types of white LEDs). In general, the term LED may refer to packaged LEDs, non-packaged LEDs, surface mount LEDs, chip-on-board LEDs, T-package mount LEDs, radial package LEDs, power package LEDs, LEDs including some type of encasement and/or optical element (e.g., a diffusing lens), etc.

The term "light source" should be understood to refer to any one or more of a variety of radiation sources, including, but not limited to, LED-based sources (including one or more LEDs as defined above), incandescent sources (e.g., filament lamps, halogen lamps), fluorescent sources, phosphorescent sources, high-intensity discharge sources (e.g., sodium vapor, mercury vapor, and metal halide lamps), lasers, other types of electroluminescent sources, pyro-luminescent sources (e.g., flames), candle-luminescent sources (e.g., gas mantles, carbon arc radiation sources), photo-luminescent sources (e.g., gaseous discharge sources), cathode luminescent sources using electronic satiation, galvano-luminescent sources, crystallo-luminescent sources, kine-luminescent sources, thermo-luminescent sources, triboluminescent sources, sonoluminescent sources, radioluminescent sources, and luminescent polymers.

A given light source may be configured to generate electromagnetic radiation within the visible spectrum, outside the visible spectrum, or a combination of both. Hence, the terms "light" and "radiation" are used interchangeably herein. Additionally, a light source may include as an integral component one or more filters (e.g., color filters), lenses, or other optical components. Also, it should be understood that light sources may be configured for a variety of applications, including, but not limited to, indication, display, and/or illumination. An "illumination source" is a light source that is particularly configured to generate radiation having a sufficient intensity to effectively illuminate an interior or exterior space. In this context, "sufficient intensity" refers to sufficient radiant power in the visible spectrum generated in the space or environment (the unit "lumens" often is employed to represent the total light output from a light source in all directions, in terms of radiant power or "luminous flux") to provide ambient illumination (i.e., light that may be perceived indirectly and that may be, for example, reflected off of one or more of a variety of intervening surfaces before being perceived in whole or in part).

The term "spectrum" should be understood to refer to any one or more frequencies (or wavelengths) of radiation produced by one or more light sources. Accordingly, the term "spectrum" refers to frequencies (or wavelengths) not only in the visible range, but also frequencies (or wavelengths) in the infrared, ultraviolet, and other areas of the overall electromagnetic spectrum. Also, a given spectrum may have a relatively narrow bandwidth (e.g., a FWHM having essentially few frequency or wavelength components) or a relatively wide bandwidth (several frequency or wavelength components having various relative strengths). It should also be appreciated that a given spectrum may be the result of a mixing of two or more other spectra (e.g., mixing radiation respectively emitted from multiple light sources).

For purposes of this disclosure, the term "color" is used interchangeably with the term "spectrum." However, the term "color" generally is used to refer primarily to a property of radiation that is perceivable by an observer (although this usage is not intended to limit the scope of this term). Accordingly, the terms "different colors" implicitly refer to multiple spectra having different wavelength components and/or bandwidths. It also should be appreciated that the term "color" may be used in connection with both white and non-white light.

The term "color temperature" generally is used herein in connection with white light, although this usage is not intended to limit the scope of this term. Color temperature essentially refers to a particular color content or shade (e.g., reddish, bluish) of white light. The color temperature of a given radiation sample conventionally is characterized according to the temperature in degrees Kelvin (K) of a black body radiator that radiates essentially the same spectrum as the radiation sample in question. Black body radiator color temperatures generally fall within a range of from approximately 700 degrees K (typically considered the first visible to the human eye) to over 10,000 degrees K; white light generally is perceived at color temperatures above 1500-2000 degrees K.

Lower color temperatures generally indicate white light having a more significant red component or a "warmer feel," while higher color temperatures generally indicate white light having a more significant blue component or a "cooler feel." By way of example, fire has a color temperature of approximately 1,800 degrees K, a conventional incandescent bulb has a color temperature of approximately 2848 degrees K, early morning daylight has a color temperature of approximately 3,000 degrees K, and overcast midday skies have a color temperature of approximately 10,000 degrees K. A color image viewed under white light having a color temperature of approximately 3,000 degree K has a relatively reddish tone, whereas the same color image viewed under white light having a color temperature of approximately 10,000 degrees K has a relatively bluish tone.

The terms "lighting fixture" or "luminaire" are used herein interchangeably to refer to an implementation or arrangement of one or more lighting units in a particular form factor, assembly, or package. The term "lighting unit" is used herein to refer to an apparatus including one or more light sources of same or different types. A given lighting unit may have any one of a variety of mounting arrangements for the light source(s), enclosure/housing arrangements and shapes, and/or electrical and mechanical connection configurations. Additionally, a given lighting unit optionally may be associated with (e.g., include, be coupled to and/or packaged together with) various other components (e.g., control circuitry) relating to the operation of the light source(s). An "LED-based lighting unit" refers to a lighting unit that includes one or more LED-based light sources as discussed above, alone or in combination with other non LED-based light sources. A "multi-channel" lighting unit refers to an LED-based or non LED-based lighting unit that includes at least two light sources configured to respectively generate different spectrums of radiation, wherein each different source spectrum may be referred to as a "channel" of the multi-channel lighting unit.

The term "controller" is used herein generally to describe various apparatus relating to the operation of one or more light sources. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

In one network implementation, one or more devices coupled to a network may serve as a controller for one or more other devices coupled to the network (e.g., in a master/slave relationship). In another implementation, a networked environment may include one or more dedicated controllers that are configured to control one or more of the devices coupled to the network. Generally, multiple devices coupled to the network each may have access to data that is present on the communications medium or media; however, a given device may be "addressable" in that it is configured to selectively exchange data with (i.e., receive data from and/or transmit data to) the network, based, for example, on one or more particular identifiers (e.g., "addresses") assigned to it.

The term "network" as used herein refers to any interconnection of two or more devices (including controllers or processors) that facilitates the transport of information (e.g. for device control, data storage, data exchange, etc.) between any two or more devices and/or among multiple devices coupled to the network. As should be readily appreciated, various implementations of networks suitable for interconnecting multiple devices may include any of a variety of network topologies and employ any of a variety of communication protocols. Additionally, in various networks according to the present disclosure, any one connection between two devices may represent a dedicated connection between the two systems, or alternatively a non-dedicated connection. In addition to carrying information intended for the two devices, such a non-dedicated connection may carry information not necessarily intended for either of the two devices (e.g., an open network connection). Furthermore, it should be readily appreciated that various networks of devices as discussed herein may employ one or more wireless, wire/cable, and/or fiber optic links to facilitate information transport throughout the network.

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, a mouse, keyboard, keypad, various types of game controllers (e.g., joysticks), track balls, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

Figure 1:
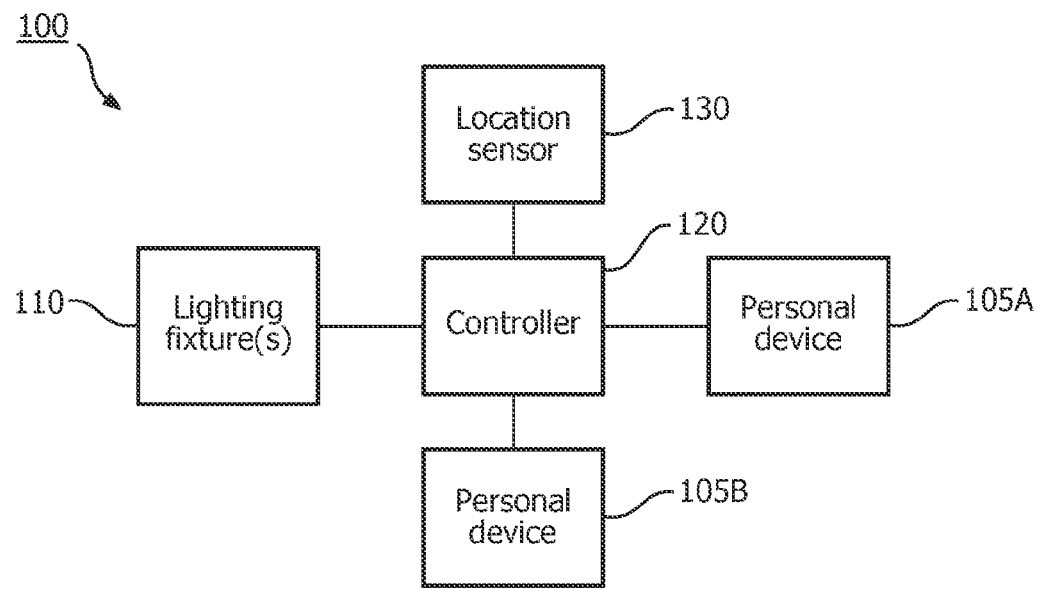
FIG. 1 illustrates a block diagram of an example lighting system in communication with two personal devices of users.

Various therapeutic lighting systems are known utilized in the art. For example, therapeutic lighting systems have been utilized as therapy for seasonal depression, therapy for jetlag by flying, therapy for social jetlag, etc. Such therapeutic lighting systems may have one or more drawbacks such as, for example, the requirement of dedicated spaces, the bright therapeutic light may be bothersome to other individuals present that do not need the light therapy, and/or the therapeutic lighting systems may not offer dynamic personalized sections for multiple users. Thus, Applicants have recognized and appreciated a need to provide methods and apparatus related to lighting control that may optionally be utilized to overcome one or more drawbacks of existing lighting systems such as existing therapeutic lighting systems.

More generally, Applicants have recognized and appreciated that it would be beneficial to provide lighting methods and apparatus for providing adaptive and dynamic personalized lighting areas.

In view of the foregoing, various embodiments and implementations of the present invention are directed to lighting control and lighting apparatus.

In the following detailed description, for purposes of explanation and not limitation, representative embodiments disclosing specific details are set forth in order to provide a thorough understanding of the claimed invention. However, it will be apparent to one having ordinary skill in the art having had the benefit of the present disclosure that other embodiments according to the present teachings that depart from the specific details disclosed herein remain within the scope of the appended claims. Moreover, descriptions of well-known apparatus and methods may be omitted so as to not obscure the description of the representative embodiments. Such methods and apparatus are clearly within the scope of the claimed invention. For example, various embodiments of the approach disclosed herein are particularly suited for a lighting system that is utilized for therapeutic purposes such as treating jetlag, social jetlag, seasonal depression, surgery recovery, etc. Accordingly, for illustrative purposes, the claimed invention is often discussed in conjunction with such a lighting system. However, other configurations and applications are contemplated without deviating from the scope or spirit of the claimed invention. For example, aspects may be implemented in other lighting systems that are not utilized in a therapy setting and/or are not configured specifically for utilization for therapeutic purposes.

It may be desirable to provide lighting having particular light output characteristics to a user. For example, it may be desirable to provide therapeutic lighting to a user for a number of purposes. For instance, international travelers are impacted seriously by jetlag and its consequences such as sleep disturbances and concentration loss. Such consequences of jetlag can have serious negative influence on the performance of these travelers. The use of bright or dimmed light according a certain time schedule dependent on the travel specifics of the traveler has been found to reduce the symptoms of the jetlag.

Different travelers to the same geographic destination may have different jetlag therapy lighting needs at the same time. For example, in some embodiments a first traveler travelling five time zones to the west to a geographic destination may have a need for exposure to bright light during a time period and a second traveler travelling thirteen time zones to the west may have a need for dimmed or no light during the same time period. Also, for example, in some embodiments the time of day during which therapeutic lighting for jetlag is applied may need to be delayed and/or advanced each day the traveler is at a geographic location. Accordingly, two travelers arriving from the same geographic origin at the same geographic destination two days apart may have different therapeutic lighting needs during different times of the day.

The particular light output characteristics of optimal light provided to a user may also depend on individual properties like age, habitual activity, and/or sleep patterns. For example, jetlag therapy may take into account sleep patterns. Also, for example, optimal reading lighting for an individual may take into account the age of that individual in setting the light output level. Also, for example, timing of pre-bedtime lighting may take into account age and/or sleep patterns. Embodiments of the lighting system described herein may maximize the exposure of an individual to light having one or more light output characteristics corresponding to the user's lighting needs. Such a lighting system may optionally be integrated as part of a general lighting system, may be implemented in various environments, and/or may provide multiple lighting profiles to multiple users within a space.

FIG. 1 illustrates a block diagram of an example lighting system 100 in communication with two personal devices 105A, 105B of two separate users. The lighting system 100 includes a controller 120 in communication with a location sensor 130 and in communication with one or more lighting fixtures 110. The controller 120 is also in communication with the personal devices 105A, 105B. In some implementations the controller 120 and/or the location sensor 130 may be integrated with one or more of the lighting fixtures 110. For example, in some embodiments multiple lighting fixtures 110 may be provided, each having a controller integrated therein and controllers across multiple lighting fixtures 110 may optionally communicate with one another. Also, for example, in some embodiments multiple lighting fixtures 110 may be provided, with one having a controller integrated therein that controls multiple lighting fixtures 110 via communication with those other lighting fixtures.

The lighting fixtures 110 may include one or more lighting fixtures that generate light with unique light output characteristics and/or that alter light output characteristics of light thereof responsive to communications from controller 120. For example, in some embodiments the lighting fixture 110 may include a first lighting fixture and a second lighting fixture. The first lighting fixture may generate a first lighting output having first light output characteristics in a first area in response to communications from controller 120. The second lighting fixture may generate a distinct second lighting output having second light output characteristics in a second area in response to communications from controller 120. In some embodiments the first and/or the second lighting fixture may have adjustable light output characteristics such as light output level, color, and/or beam shape. The area(s) in which a lighting fixture provides light output may be fixed (e.g., as a function of the installation location of the lighting fixtures) or may be adjustable. Adjustability of the areas in which a lighting fixture provides light output may be achieved utilizing one or more of a variety of methods and/or apparatus. For example, adjustability may be achieved by turning on/off one of multiple light sources in the lighting fixture; by mechanically adjusting the position and/or orientation of the entire lighting fixture; and/or by mechanically adjusting the position and/or orientation of a light source and/or an optical element (e.g., a reflector, a refractor) of the lighting fixture.

In some implementations, the lighting fixtures 110 may include a LED-based lighting fixture having a plurality of LEDs that may be individually turned on/off, individually dimmed, and/or individually tuned (e.g., tunable color, beam shape, beam size). A first group of the LEDs of the LED-based lighting fixture may be adjusted to achieve a light output having first light output characteristics and a second LED group of the LED-based lighting fixture may be adjusted to achieve a light output having second light output characteristics. In some embodiments the lighting fixtures 110 may include a plurality of light emitting ceiling tile groups, with each group containing one or more tiles (e.g., tiles with implemented LEDs) and having a unique lighting setting. Examples of specific lighting fixture implementations are provided herein. One of ordinary skill in the art, having had the benefit of the present disclosure, will recognize and appreciate that in other embodiments additional and/or alternative lighting fixtures may be utilized in the lighting systems and/or lighting methods described herein.

The location sensor 130 may include one or more sensors utilized to determine the location of one or more users. For example, the location sensor 130 may include one or more radars, cameras, distance sensors, and/or PIR sensors. For example, a radar may be utilized to detect the location of the personal device 105A (e.g., based on detection of RF signals emitted by the personal device and/or RF signals emitted by the radar) and it may be assumed that the location of the personal device 105A corresponds to the location of a first user. Also, for example, a camera and a distance sensor may be utilized to identify a location of a particular user based on facial recognition and a distance reading from the distance sensor. In some embodiments the location sensor 130 may be omitted. For example, in embodiments of the lighting system 100 that implement the method of FIG. 3, the location sensor 130 may optionally be omitted. Also, for example, in embodiments of the lighting system 100 location data may be received via input from personal devices 105A, 105B (e.g., via a GPS device and/or other location device of the personal devices 105A, 105B) and the location sensor 130 may optionally be omitted.

In some embodiments, the personal devices 105A, 105B may include a lighting token carried by a user that enables communication of information relevant to the lighting needs of the user. For example, in some embodiments the personal devices 105A, 105B may include a RFID tag carried by the user that may be read by a RFID receiver to identify the lighting needs of the user. For instance, the RFID tag may communicate the identity of the user to the controller 120. The controller 120 may utilize the identity of the user to retrieve therapeutic lighting settings that are correlated with the user in a database (local database and/or a database accessible via a network). Also, for instance, the RFID tag may communicate the identity of the user to the controller 120; the controller 120 may utilize the identity of the user to retrieve travel history and/or travel plans of the user that are correlated with the user in a database; and based on such travel history and/or travel plans the controller 120 may identify the therapeutic lighting needs of the user.

In some embodiments, the personal devices 105A, 105B may include a smart phone, a tablet computer, and/or other handheld device capable of performing additional functions beyond those described herein. For example, the personal devices 105A, 105B may include a smart phone that communicates therapeutic lighting needs to the controller 120 (either directly or via the supplying of travel itinerary information). In some embodiments the personal devices 105A, 105B may additionally or alternatively communicate location information to the controller 120. For example, the location may be determined at the personal devices 105A, 105B via GPS and/or RF triangulation and such location communicated to the controller 120.

In some embodiments, the personal devices 105A, 105B may include a display that provides an indication to the user of an area where lighting settings appropriate to the user are available. For example, the display may show a floor plan of the space in which the user is located and highlight areas of the floor plan in which the user may obtain lighting settings that are appropriate for the user. Also, for example, the display may show an interface that provides indication of a direction and/or distance the user needs to move to obtain lighting settings that are appropriate for the user.

In some embodiments, the personal devices 105A, 105B may include a light sensor to sense if the appropriate lighting effect is present. The readings from the light sensor may optionally be communicated to the controller 120 to optionally modify the light output directed toward the user's location to achieve a desired light output. The readings from the light sensor may optionally be utilized to inform the user via the personal devices 105A, 105B whether the light at the location is appropriate for the user. Also, in some embodiments the readings from the light sensor may be tracked over time and optionally be utilized to determine whether appropriate light effects have been received in a timely manner by the user and, if not, the user may optionally be notified and/or presented with options for obtaining the appropriate light effect (e.g., where to move to get the appropriate light output).

The communication between the various components of the lighting system 100 and/or other devices (e.g., personal devices 105A, 105B) may optionally utilize one or more communications mediums, communications technologies, protocols, and/or inter-process communication techniques. For example, the communication mediums may include any physical medium, including, for example, twisted pair coaxial cables, fiber optics, and/or a wireless link using, for example, infrared, microwave, or encoded visible light transmissions and any suitable transmitters, receivers or transceivers to effectuate communication in the lighting fixture network. Also, for example, the communications technologies may include any suitable protocol for data transmission, including, for example, TCP/IP, variations of Ethernet, Universal Serial Bus, Bluetooth, FireWire, Zigbee, DMX, Dali, 802.11b, 802.11a, 802.11g, token ring, a token bus, serial bus, power line networking over mains or low voltage power lines, and/or any other suitable wireless or wired protocol. For example, in some embodiments the personal devices 105A, 105B may communicate with the controller 120 via RF communications and the controller 120 may communicate with lighting fixtures 110, and/or location sensor 130 via a wired connection.

Figure 2:
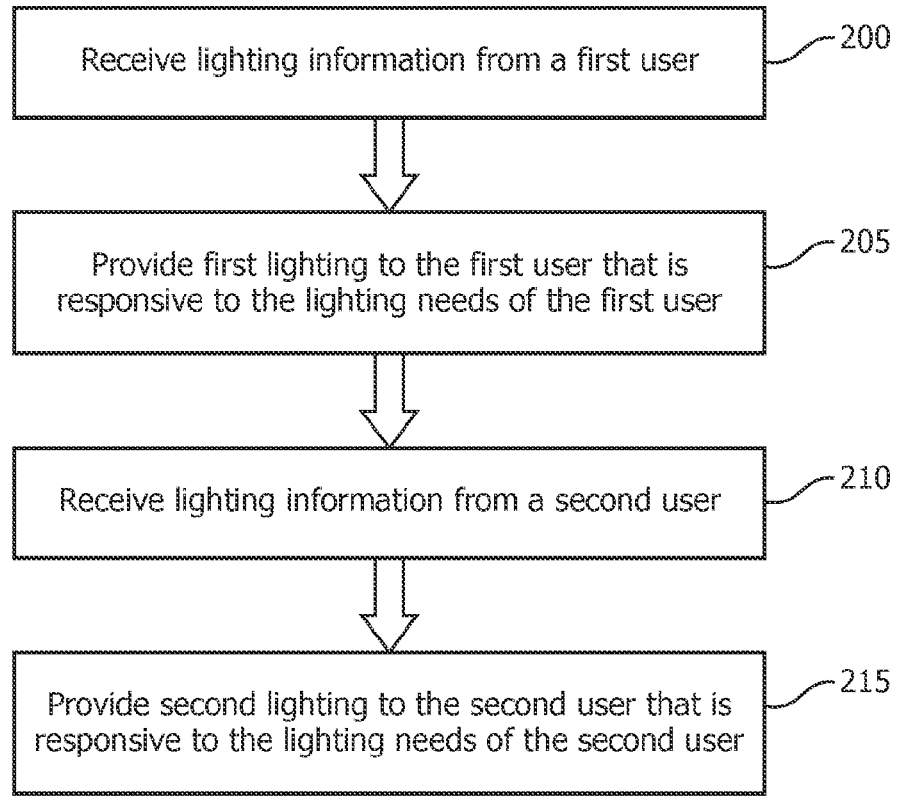
FIG. 2 is a flow chart illustrating an embodiment of a method of controlling lighting provided to multiple users.

FIG. 2 is a flow chart illustrating an embodiment of a method of controlling lighting provided to multiple users. Other embodiments may perform the steps in a different order, omit certain steps, and/or perform different and/or additional steps than those illustrated in FIG. 2. In some embodiments one or more controllers and/or lighting fixtures, such as the controller 120 and/or the lighting fixture 110 of FIG. 1 may perform the steps of FIG. 2.

At step 200 lighting information is received from a first user. For example, the controller 120 may receive lighting information directly from first personal device 105A. Also, for example, the controller 120 may receive the lighting information directly from a remote computing device. For instance, when making a reservation at a hotel the user may enter information (e.g., user home time zone, length of stay, user preferences, and/or user age) that may be utilized to determine lighting information for that user that may then be transmitted to the controller 120. Also, for example, the controller 120 may receive travel information from first personal device 105A and utilize such travel information to determine appropriate lighting information.

Also, for example, the controller 120 may receive user identification information from first personal device 105A and utilize such identification information to receive lighting information pertinent to the user. For example, the user identification information may be utilized to obtain lighting information for the user directly from a database. Also, for example, the user identification information for the user may be utilized to identify information about the user that may then be utilized to determine appropriate light settings for the user. For instance, a user's travel itinerary may be utilized to determine light settings that may be appropriate for treating jetlag. Also, for example, demographic information obtained from a hotel database, meeting database, etc. may be utilized to determine how many time zones the user is away from home, when the user checked-in, how old the user is, etc. to determine light settings that may be appropriate for the user's situation. For instance, teenagers may have a strong evening preference and go to bed late and have difficulties waking in the morning. Accordingly, light settings for the teenager may include bright and/or cooler light in the morning to reduce their sleep inertia in the morning and assist in the wake up process. Also, for example habitual information for the user obtained from a database (e.g., habitual bedtime information obtained via user input and/or from home automation signals such as light/water/room usage signals) may be utilized to determine light settings that may be appropriate for the user.

At step 205 first lighting is provided to the first user that is responsive to the lighting needs of the first user. For example, the controller 120 may direct one of the lighting fixtures 110 to provide lighting that is responsive to the lighting needs of the first user. For instance, if the time is near the first user's habitual bedtime, the controller 120 may direct one of the lighting fixtures providing lighting to the first user to dim the light output to a low level. In some embodiments the lighting specific to the first user may be directed specifically toward the location of the first user. For example, in some embodiments the location of the first user may be obtained (e.g., via location sensor 130 and/or via location information received from personal device 105A) and light directed specifically toward that location. For example, the lighting fixture 110 that is directed to provide lighting that is responsive to the lighting needs of the first user may be chosen because it provides a light output directed specifically toward that location. Also, for example, only certain light sources of one or more lighting fixtures may provide lighting that is responsive to the lighting needs of the first user and the certain light sources may be chosen because they provide light output directed specifically toward that location. Also, for example, one or more lighting fixtures may be mechanically redirectable and provide lighting that is responsive to the lighting needs of the first user and the certain lighting fixtures redirected to provide light output directed specifically toward that location.

In some embodiments the lighting specific to the first user may be directed toward one or more areas and the first user may be instructed that the lighting is available in those one or more areas. For example, in some embodiments lighting that meets the lighting needs of the first user may be directed toward one area of a space and the user may be directed to that area. For example, the first user may be directed to that area via a graphical display on the first user's personal device 105A and/or via audio instructions from the first user's personal device 105A.

At step 210 lighting information is received from a second user. For example, the controller 120 may receive lighting information directly from second personal device 105B. Also, for example, the controller 120 may receive travel information from second personal device 105B and utilize such travel information to determine appropriate lighting information. Also, for example, the controller 120 may receive user identification information from second personal device 105B and utilize such user identification information to receive lighting information pertinent to the user. Also, for example, demographic information obtained from a hotel database, meeting database, etc. may be utilized to determine how many time zones the user is away from home, how old the user is, etc. to determine light settings that may be appropriate for the user's situation. Also, for example habitual information for the user obtained from a database may be utilized to determine light settings that may be appropriate for the user.

At step 215 second lighting is provided to the second user that is responsive to the lighting needs of the second user. The characteristics of the first lighting of step 205 and the second lighting of step 215 may be distinct from one another over one or more time periods. For example, the first lighting may be bright therapeutic lighting over a time period whereas the second lighting may be dim therapeutic lighting during the same time period. In some embodiments the controller 120 may direct one of the lighting fixtures 110 to provide lighting that is responsive to the lighting needs of the first user. In some embodiments the lighting specific to the second user may be directed specifically toward the location of the second user. In some embodiments the lighting specific to the second user may be directed toward one or more areas and the second user may be instructed that the lighting is available in those one or more areas.

In some embodiments, two users having different lighting needs may both be present in an area in which only a single group of light settings may be applied. For example, a younger person and an older person may both be sitting on a reading couch in a first area. The older person may need brighter lighting than the younger person and only one lighting setting may be applied to the first area. Priority rules and/or accommodation rules may optionally be implemented to address such situations. For example, a priority rule may be implemented wherein the brighter lighting is applied in such a conflicting situation. Also, for example, an accommodation rule may be applied wherein the lighting applied is a middle ground between the preferred lighting settings of the younger person and the older person.

Figure 3:
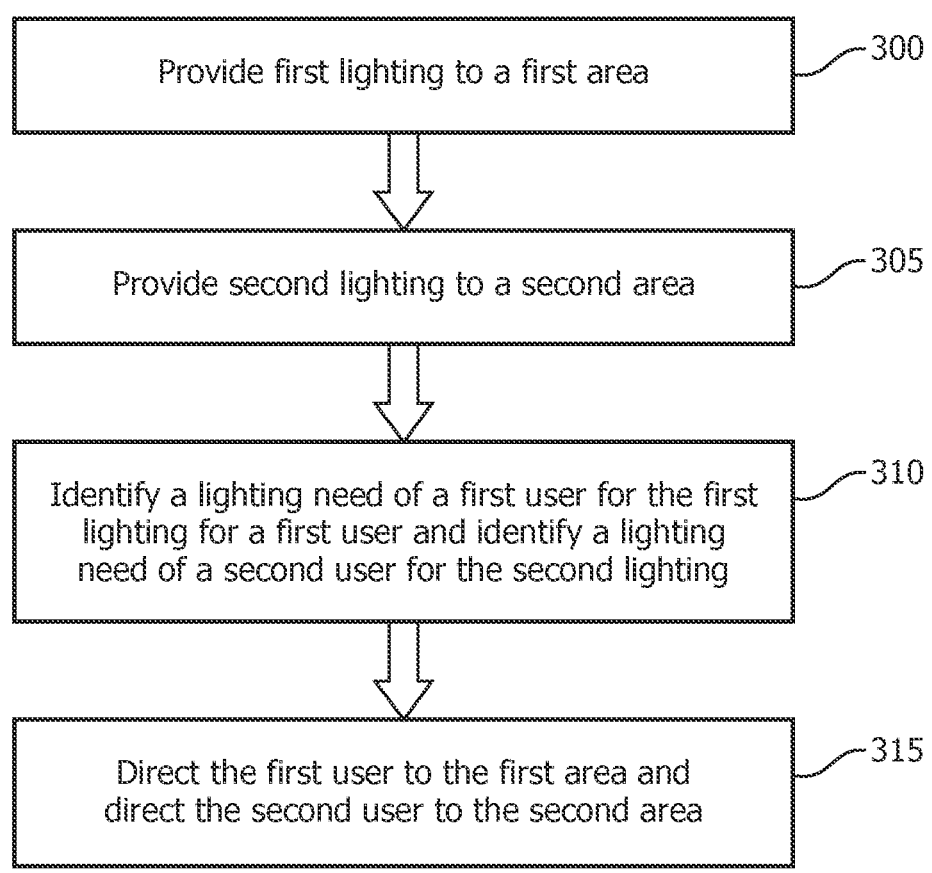
FIG. 3 is a flow chart illustrating another embodiment of a method of controlling lighting provided to multiple users.

FIG. 3 is a flow chart illustrating another embodiment of a method of controlling lighting provided to multiple users. Other embodiments may perform the steps in a different order, omit certain steps, and/or perform different and/or additional steps than those illustrated in FIG. 3. In some embodiments one or more controllers and/or lighting fixtures, such as the controller 120 and/or the lighting fixture 110 of FIG. 1 may perform the steps of FIG. 3.

At step 300 first lighting is provided to a first area. For example, the controller 120 may direct one of the lighting fixtures 110 to provide lighting that is responsive to the lighting needs of one or more users to a first area within a space.

At step 305 second lighting is provided to a second area that is distinct from the first area. For example, the controller 120 may direct one of the lighting fixtures 110 to provide lighting that is responsive to the lighting needs of one or more users to a second area within the space. In some embodiments the first lighting and the second lighting have one or more of distinct light output intensity, distinct color, and distinct dynamic behavior. For example, the first light output characteristics of the first lighting may be static over a period of time and the second light output of the second lighting may be dynamic and change in light output intensity and/or spectral composition over the same period of time.

At step 310 a lighting need of the first user for the first lighting is identified and a lighting need of the second user for the second lighting is identified. For example, the controller 120 may receive lighting information directly from first personal device 105A and/or the second personal device 105B and identify the lighting needs of the users based on such lighting information. Also, for example, the controller 120 may receive travel information from the first personal device 105A and/or second personal device 105B (e.g., as indicated by recorded changing GPS coordinates) and utilize such travel information to determine lighting needs of the users based on such information. Also, for example, the controller 120 may receive user identification information from the first personal device 105A and/or the second personal device 105B and utilize such identification information to receive lighting information pertinent to the user. Also, for example, demographic information obtained from a hotel database, meeting database, etc. may be utilized to determine how many time zones the user is away from home, how old the user is, etc. to determine light settings that may be appropriate for the user's situation. Also, for example habitual information for the user obtained from a database may be utilized to determine light settings that may be appropriate for the user.

In some implementations, step 310 may occur before step 300 and/or step 305. For example, in some implementations the first lighting may be initially configured and/or provided in response to identification of the lighting need of the first user and/or the second lighting may be initially configured and/or provided in response to identification of the lighting need of the second user. In some implementations a gradually transitioning lighting profile may be provided in a space between the first lighting and the second lighting. The gradually transitioning lighting profile may include the first lighting in one area, the second lighting in a second area, and a plurality of gradually transitioning lighting profile areas between the first area and the second area.

At step 315 the first user is directed to the first area and the second user is directed to the second area. For example, the first user may be directed to the first area via a graphical display on the first user's personal device 105A and/or via audio instructions from the first user's personal device. Also, for example, the second user may be directed to the second area via a graphical display on the second user's personal device 105B and/or via audio instructions from the second user's personal device.

Figure 4:
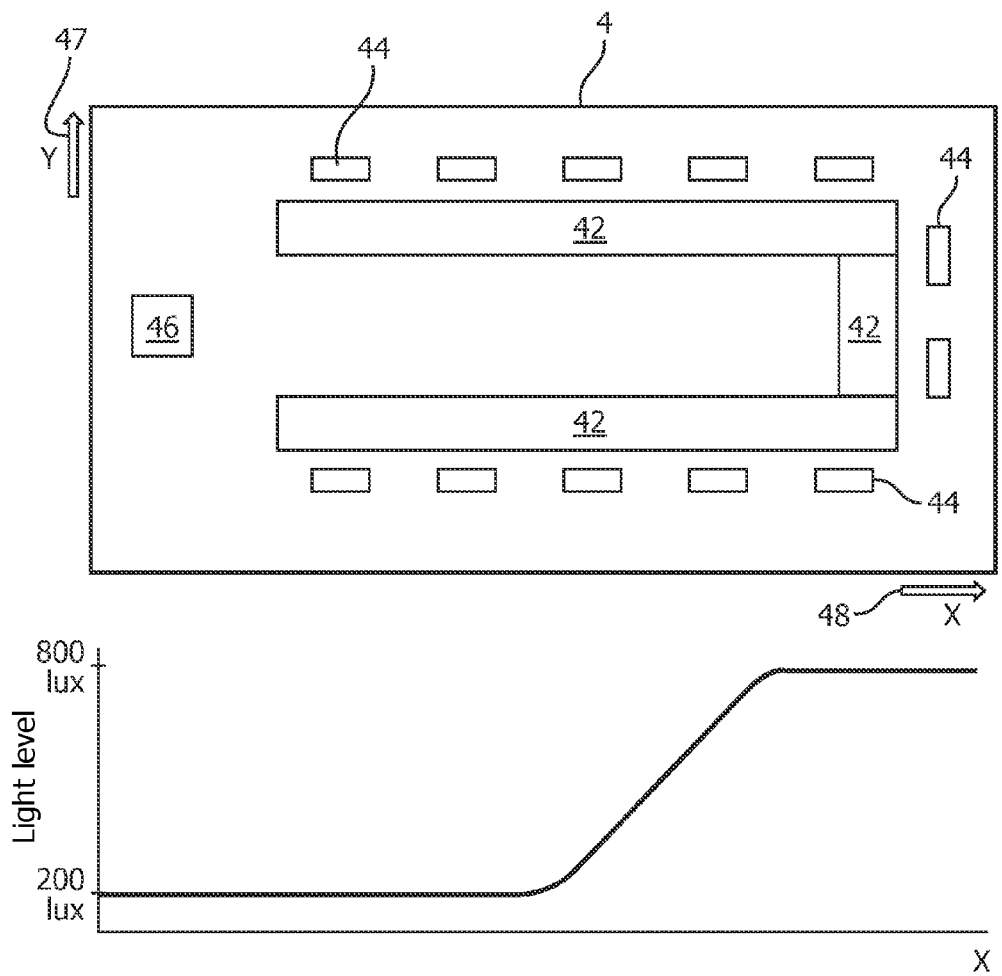
FIG. 4 illustrates a top plan view of a meeting room having an embodiment of a lighting system and a chart illustrating the light level provided by the lighting system at various positions in the meeting room.

FIG. 4 illustrates a top plan view of a meeting room 4 having an embodiment of a lighting system and a chart illustrating the light level provided by the lighting system at various positions in the meeting room 4. The meeting room 4 includes three tables 42 arranged in a U shape in the room and twelve chairs 44 positioned exteriorly of the tables 42. A presentation area 46 is provided at the open end of the tables 42. A Y direction 47 of the meeting room 4 is indicated in FIG. 4 by arrow 47 and an X direction in the meeting room 4 is indicated in FIG. 4 by arrow 48. The chart in FIG. 4 is to scale with the meeting room 4 in the X direction and illustrates the light level for changing positions in the X direction in the meeting room 4 at a fixed position in the Y direction. In some embodiments the light level illustrated in the chart is substantially the same for all positions in the Y direction. As illustrated, the light output is set to have a light level of approximately 200 lux in a first area from the leftmost portion of the meeting room 4 to approximately the half-way point of the meeting room 4 in the X direction. The light level gradually increases from approximately the half-way point of the meeting room 4 to approximately the three-fourths point of the meeting room 4 in the X direction having a plurality of gradually increasing lux values. The light level over the last fourth of the meeting room 4 is set to approximately 800 lux. In some embodiments it may be desirable to have lower light levels proximal the presentation area 46 (e.g., when a projection screen and/or a TV are utilized in the presentation area 46) and higher light levels distal the presentation area 46.

In some embodiments, methods and/or apparatus described herein may be utilized to direct users to one or more locations within the meeting room 4 according to the user's lighting needs. For example, a first user needing bright lighting may be directed to sit in those chairs 44 that are in the second area with approximately 800 lux on the rightmost side in the X direction. A second user needing dim lighting may be directed to sit in those chairs 44 that are in the first area with approximately 200 lux on the left half in the X direction. In some embodiments the first user may be directed via personal device 105A and/or the second user may be directed via personal device 105B.

Figure 5:
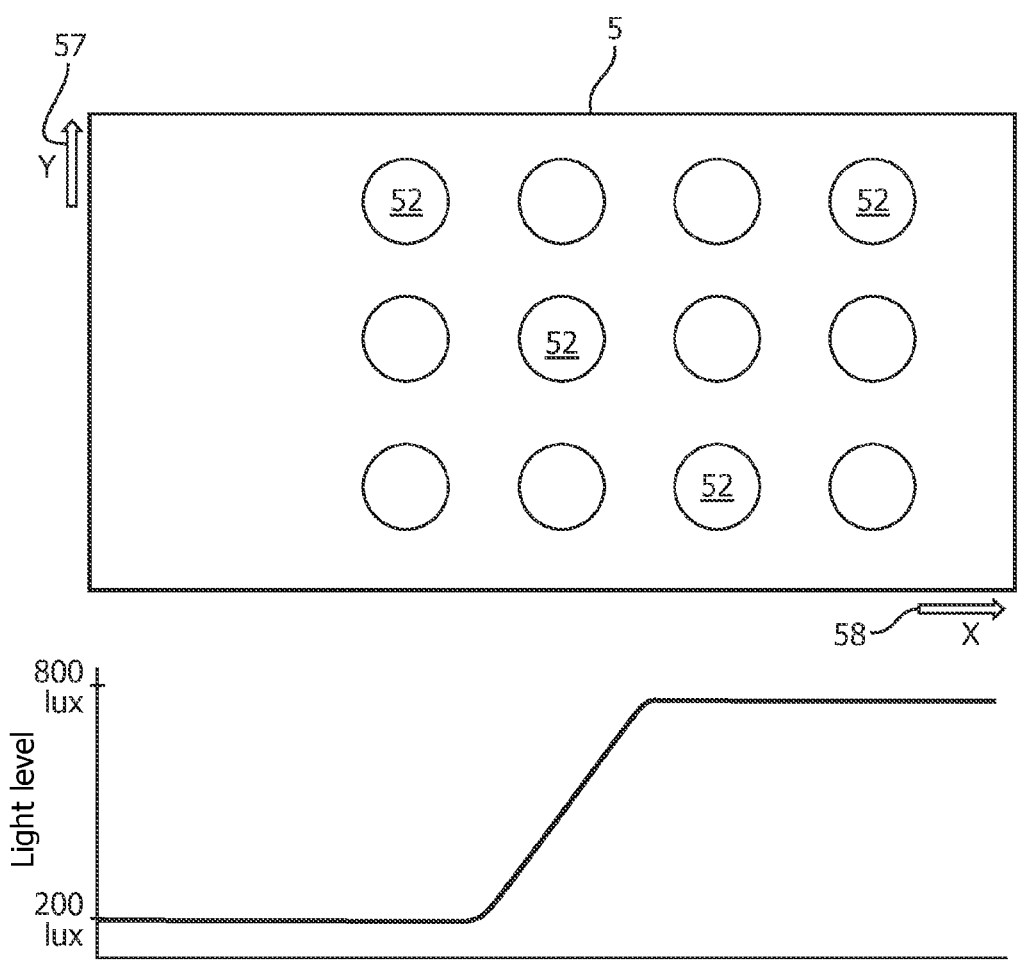
FIG. 5 illustrates a top plan view of a restaurant having an embodiment of a lighting system and a chart illustrating the light level provided by the lighting system at various positions in the restaurant.

FIG. 5 illustrates a top plan view of a restaurant 5 having an embodiment of a lighting system and a chart illustrating the light level provided by the lighting system at various positions in the restaurant 5. The restaurant 5 includes twelve tables 52 arranged in a four by three grid. A Y direction 57 of the restaurant 5 is indicated in FIG. 5 by arrow 57 and an X direction in the restaurant 5 is indicated in FIG. 5 by arrow 58. The chart in FIG. 5 is to scale with the restaurant 5 in the X direction and illustrates the light level for changing positions in the X direction in the restaurant 5 at a fixed position in the Y direction. In some embodiments the light level illustrated in the chart is substantially the same for all positions in the Y direction. As illustrated, the light output is set to have a light level of approximately 200 lux in a first area in the X direction from the leftmost portion of the restaurant 5 through approximately the first column of tables 52. The light level gradually increases in the X direction from approximately right after the first column of tables 52 to approximately right before the third column of tables 52. The light level over the last two columns of tables 52 in the restaurant 5 is set to approximately 800 lux.

In some embodiments, methods and/or apparatus described herein may be utilized to direct users to one or more locations within the restaurant 5 according to the user's lighting needs. For example, a first user needing bright lighting may be directed to sit at a table 52 that is in the second area with approximately 800 lux and a second user needing dim lighting may be directed to sit at a table 52 that is in the first area with approximately 200 lux. In some embodiments a restaurant host may be informed of the user's decision via a computing device or otherwise and direct the user to the appropriate table 52.

In other embodiments, light level may be adjusted between other lux values. For example, in some embodiments the light level may be adjusted between 100 and 2000 lux. In some embodiments warm color temperatures (e.g., 2700-3000 K) may be provided at low light levels, with increasing color temperature with increasing light level up to, for example, 6000 K at 2000 lux. In some embodiments the color temperature may follow the Kruithof curve. In some embodiments additional light areas may be provided. For example, in some embodiments first, second, and third light areas may be provided, each optionally with a gradually transitioning area in between. One or more users may optionally be directed to appropriate of the light areas based on lighting needs of the users. For example, a first user may be directed to the first light area, a second user may be directed to the second light area, and third, fourth, and fifth users may be directed to the third light area.

Figure 6:
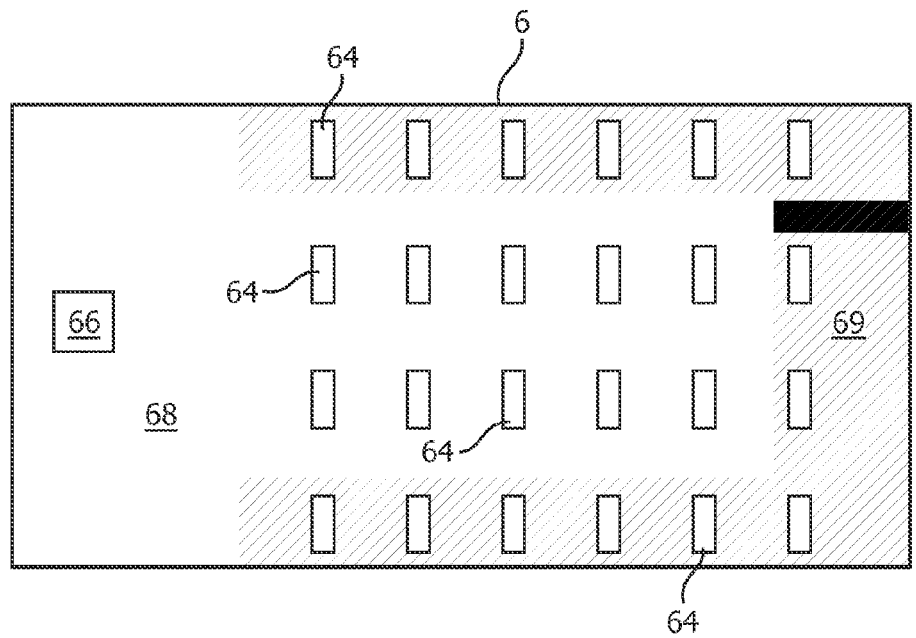
FIG. 6 illustrates a top plan view of a meeting room having an embodiment of a lighting system; different shading illustrates different lighting characteristics provided by the lighting system at various positions in the meeting room.

FIG. 6 illustrates a top plan view of a meeting room 6 having an embodiment of a lighting system. The meeting room 6 includes twenty four chairs arranged in a six by four grid. A presentation area 66 is also provided. Different shading illustrates different lighting characteristics provided by the lighting system at various positions in the meeting room. A first lighting area having first lighting characteristics is indicated by shading area 69 and a second lighting area having second lighting characteristics is indicated by no shading area 68.

In some implementations the shading area 69 may indicate a first area having relatively dim light output characteristics and no shading area 68 may indicate a second area having relatively bright light output characteristics. In some embodiments a steep transition between the relatively dim light output and the relatively bright light output may be present. In some embodiments a gradual transition between the relatively dim light output and the relatively bright light output may be present. In some embodiments methods and/or apparatus described herein may be utilized to direct users to one or more locations within the meeting room 6 according to the user's lighting needs.

Figure 7:
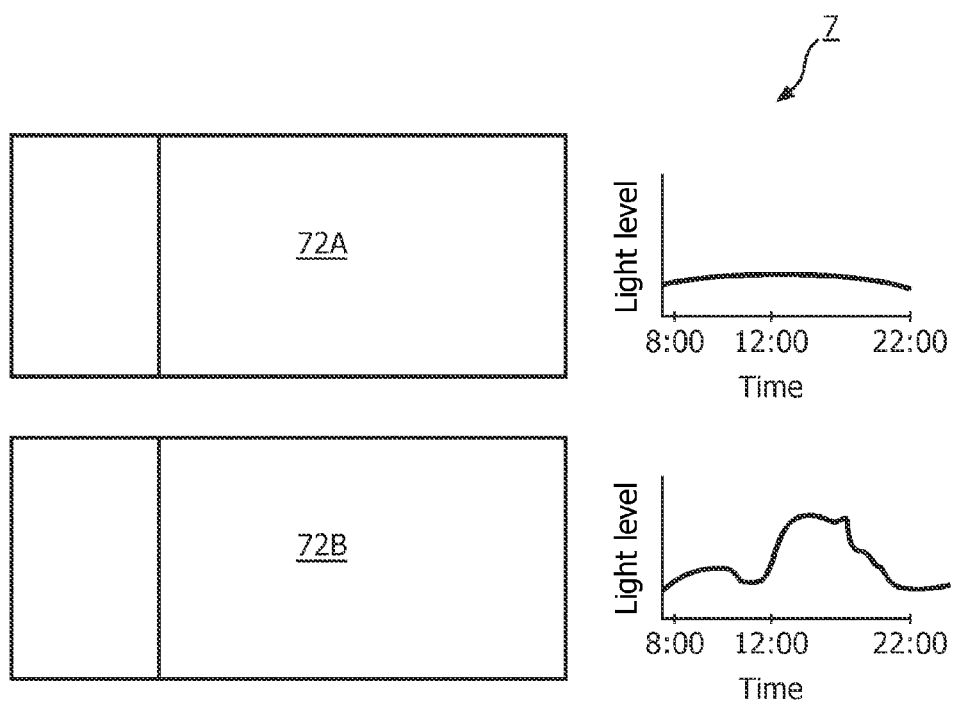
FIG. 7 illustrates a top plan view of a hospital room having two beds and an embodiment of a lighting system; a chart is illustrated at the end of each bed illustrating the light level provided by the lighting system to that bed over a period of time.

FIG. 7 illustrates a top plan view of a hospital room 7 having two beds 72A, 72B and an embodiment of a lighting system. A chart is illustrated at the end of each bed 72A, 72B illustrating the light level provided by the lighting system to that bed over a period of time. As illustrated, bed 72A is provided with relatively dim light that gradually dynamically changes, but remains relatively consistent over the illustrated time period. Bed 72B is provided with light that dynamically changes throughout the day and has relatively high light levels between the hours of approximately 12:00 and 18:00. In some embodiments the individualized light settings may be applied to and around the bed of one patient only, not to disturb the other patient and/or visitors in the room. In some embodiments individual light scenarios can be prescribed, that depend on time elapsed since medical surgery, and that are optionally maintained when patients are moved from one room to another. In some embodiments a patient may be prescribed to be exposed to dim light conditions during the first day(s) directly after surgery, while a patient who is recovered further receives more bright light conditions during at least part of the day. Such day rhythms and their change during sequential days can be prescribed per patient and applied according to one or more methods and/or apparatus described herein.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

Reference numerals appearing in the claims, if any, are provided merely for convenience and should not be construed as limiting in any way.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of controlling lighting to tailor the lighting to multiple users, comprising:
    providing first lighting having first light output characteristics to a first area in a room and providing second lighting having second light output characteristics to a second area in said room;
    wherein said first lighting and said second lighting are distinct;
    identifying lighting needs of a first user for said first light output characteristics and identifying lighting needs of a second user for said second light output characteristics; and
    directing, via a personal device of said first user, said first user to move to said first area based on identifying said lighting needs of said first user for said first light output characteristics, and directing, via a personal device of said second user, said second user to move to said second area based on identifying said lighting needs of said second user for said second light output characteristics, wherein said personal devices of said users are in communication with a controller configured to control said first lighting and said second lighting.

2. The method of claim 1, wherein said first light output characteristics include a first light output intensity level, wherein second light output characteristics include a second light output intensity level, and wherein said first light output intensity level is greater than second light output intensity level.

3. The method of claim 1, further comprising providing a smoothly transitioning lighting between said first area and said second area, said smoothly transitioning lighting gradually transitioning differences between said first light output characteristics and said second light output characteristics.

4. The method of claim 3, wherein said first light output characteristics include a first light output intensity level, wherein second light output characteristics include a second light output intensity level, and wherein said first light output intensity level is greater than second light output intensity level.

5. The method of claim 3, further comprising identifying lighting needs of a second user for said second light output characteristics and directing said second user to said second location area.

6. The method of claim 5, wherein said first lighting is dynamic and responsive to lighting needs of said first user as determined via said first user lighting information; and wherein said second lighting is dynamic and responsive to lighting needs of said second user as determined via said second user lighting information.

7. The method of claim 1, wherein said directing of said first user to said first area includes transmitting said first area to said personal device of said first user.

8. The method of claim 1, wherein said first lighting is dynamic and responsive to lighting needs of said first user as determined via said first user lighting information; and wherein said second lighting is dynamic and responsive to lighting needs of said second user as determined via said second user lighting information.

9. The method of claim 1, wherein identifying said lighting needs of said first user includes determining said lighting needs based on first user lighting information transmitted from said personal device of said first user.

10. The method of claim 9, wherein said first user lighting information is transmitted from said personal device of said first user subsequent to providing said first lighting having said first light output characteristics to said first area in said room.

11. The method of claim 1, wherein said room is one of a meeting room and a hospital room.

12. A method of controlling lighting provided to multiple users, comprising:
    receiving first user lighting information indicative of first lighting needs of a first user;
    receiving second user lighting information indicative of second lighting needs of a second user, wherein said first lighting needs of the first user are distinct from said second lighting needs of said second user;
    determining the locations of said first user and said second user;
    identifying said first user and said second user both being present in an area in which only one group of light output characteristics may be applied to said area;
    selecting light output characteristics to provide to said area based on comparison of said first lighting needs of said first user to said second lighting needs of said second user; and
    providing lighting having said light output characteristics to said area.

13. The method of claim 12, wherein selecting said light output characteristics to provide to said area based on comparison of said first lighting needs to said second lighting needs includes selecting said light output characteristics to conform with one of said first lighting needs and said second lighting needs.

14. The method of claim 12, wherein selecting said light output characteristics to provide to said area based on comparison of said first lighting needs to said second lighting needs includes selecting said light output characteristics based on determining a middle ground between said first lighting needs and said second lighting needs.

15. A lighting system for controlling lighting to tailor lighting to multiple users, comprising:
   a first lighting fixture having first light output characteristics to a first area in a room;
   a second lighting fixture having second light output characteristics to a second area in said room, wherein said first lighting and said second lighting are distinct; and
   a controller configured to identify lighting needs of a first user for said first light output characteristics and a second user for said second light output characteristics; characterized in that:
   the controller is further configured to direct, via a personal device of said first user, said first user to said first area based on identifying said lighting needs of said first user for said first light output characteristics, and direct, via a personal device of said second user, said second user to said second area based on identifying said lighting needs of said second user for said second light output characteristics.

* * * * *